US009247875B2

(12) United States Patent
Gaillard et al.

(10) Patent No.: US 9,247,875 B2
(45) Date of Patent: Feb. 2, 2016

(54) BIOMARKERS OF INFLAMMATION IN BRUCH'S MEMBRANE OF THE HUMAN RETINA

(75) Inventors: Elizabeth R. Gaillard, DeKalb, IL (US); James P. Dillon, New York, NY (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 691 days.

(21) Appl. No.: 12/753,394

(22) Filed: Apr. 2, 2010

(65) Prior Publication Data
US 2011/0244504 A1 Oct. 6, 2011

(51) Int. Cl.
*A61B 3/12* (2006.01)
*G01N 33/92* (2006.01)
*G01N 33/68* (2006.01)

(52) U.S. Cl.
CPC ............... *A61B 3/12* (2013.01); *A61B 3/1241* (2013.01); *G01N 33/6812* (2013.01); *G01N 33/92* (2013.01); *G01N 2800/164* (2013.01); *G01N 2800/52* (2013.01); *G01N 2800/56* (2013.01)

(58) Field of Classification Search
CPC ...... A61N 5/1017; A61B 3/12; A61B 3/1241; A61B 3/13
See application file for complete search history.

(56) References Cited

U.S. PATENT DOCUMENTS

| 6,355,623 B2 * | 3/2002 | Seidman et al. ................. 514/45 |
| 2003/0004418 A1 * | 1/2003 | Marmorstein ................. 600/475 |

OTHER PUBLICATIONS

Fan et al. (Clin. Biochem. 2006 39:231-239).*
Boyd (The Basic Science of Oncology, 1992, McGraw-Hill, Inc., p. 379).*
Murdaugh et al. (Exper. Eye. Res. Feb. 12, 2010 90:564-571).*
Ahmadi et al. (Expert Opin. Pharmcother. 2008 9 (17): 3045-3052).*
Albert et al. (Arch. Ophthalmol. Feb. 2010 128(2): 212-222).*
Suh et al. (FASEB J. Apr. 2007 21(5): A235-A236).*
Sparrow et al. (Invest. Ophthalmology & Visual Sci. Nov. 1999, 40(12): 2988-2995).*
Anderson et al., "A role for local inflammation in the formation of drusen in the aging eye," *Am. J. Ophthalmol.*, 134: 411-431 (2002).
Bailey et al., "Mechanisms of maturation and ageing of collagen," *Mech. Ageing Dev.*, 106: 1-56 (1998).
Booij et al., "The dynamic nature of Bruch's membrane," *prog. Retin. Eye Res.*,29(1): 1-18 2010.
Borland et al., "Nitric oxide yields of contemporary UK, US and French cigarettes," *Int. J. Epidemiol.*, 16:1 31-34 (1987).
Carreras et al., "Kinetics of nitric oxide and hydrogen peroxide production and formation of peroxynitrite during the respiratory burst of human neutrophils," *FEBS Letters*, 341: 65-68 (1994).
Chen et al., "Synthesis of complement factor H by retinal pigment epithelial cells is down-regulated by oxidized photoreceptor outer segments," *Exp. Eye Res.*, 84: 635-645 (2007).
Crabb et al., "Drusen proteome analysis: an approach to the etiology of age-related macular degeneration," *Proc. Natl. Acad. Sci. USA*, 99:23 14682-14687 (2002).
Crane et al., "Mechanisms of leukocyte migration across the blood-retina barrier," *Semin Immunopathol.*, 30: 165-177 (2008).
Crowley et al., "Isotope dilution mass spectrometric quantification of 3-nitrotyrosine in proteins and tissues is facilitated by reduction to 3-aminotyrosine," *Anal. Biochem.*, 259: 127-135 (1998).
Del Priore et al., "Reattachment rate of human retinal pigment epithelium to layers of human Bruch's membrane," *Arch. Ophthalmol.*, 116: 335-341 (1998).
Di Stasi et al., "Peroxynitrite induces tyrosine nitration and modulates tyrosine phosphorylation of synaptic proteins," *J. Neurochem.*, 73: 727-735 (1999).
Dillon et al., "The photochemical oxidation of A2E results in the formation of a 5,8,5',8'-bis-furanoid oxide," *Exp. Eye Res.*, 79: 537-542 (2004).
Dua et al., "Ultrastructural pathology of the 'barrier sites' in experimental autoimmune uveitis and experimental autoimmune pinealitis," *Br. J. Ophthalmol.*, 75: 391-397 (1991).
Edwards et al., "Complement factor H polymorphism and age-related macular degeneration," *Science*, 308: 421-424 (2005).
El-Remessy et al., "Experimental diabetes causes breakdown of the blood-retina barrier by a mechanism involving tyrosine nitration and increases in expression of vascular endothelial growth factor and urokinase plasminogen activator receptor," *Am. J. Pathol.*, 162:6 1995-2004 (2003).
Erickson et al., "Vascular permeability in ocular disease and the role of tight junctions," *Angiogenesis*, 10: 103-117 (2007).
Evereklioglu et al., "Nitric oxide and lipid peroxidation are increased and associated with decreased antioxidant enzyme activities in patients with age-related macular degeneration," *Doc. Ophthal. Mol.*, 106: 129-136 (2003).
Farrell et al., "Increased concentrations of nitrite in synovial fluid and serum samples suggest increased nitric oxide synthesis in rheumatic diseases," *Ann. Rheum. Dis.*, 51: 1219-1222 (1992).
Feeney-Burns et al., "Age-related changes in the ultrastructure of Bruch's membrane," *Am. J. Ophthalmol.*, 100: 686-697 (1985).
Feeney-Burns et al., "Lysosomal enzyme cytochemistry of human RPE, Bruch's membrane and drusen," *Invest. Ophthalmol. Vis. Sci.*, 28: 1138-1147 (1987).

(Continued)

*Primary Examiner* — Peter J Reddig
(74) *Attorney, Agent, or Firm* — Barnes & Thornburg LLP; Alice O. Martin

(57) ABSTRACT

A method of diagnosing a patient with age-related macular degeneration (AMD), by detecting biomarkers in the patient's Bruch's membrane, and diagnosing the patient with AMD. A method of detecting the presence of AMD in a patient, by detecting biomarkers in the patient's Bruch's membrane. A method of detecting inflammation in a patient, by detecting biomarkers in the patient's Bruch's membrane. A method of determining the progression of AMD in a patient. A method of determining efficacy of a treatment for AMD in a patient. A method of determining the presence of AMD in an animal model. A kit for detecting the presence of disease in a patient, including an assay for biomarkers 3-nitrotyrosine and nitro-A2E. An assay of the biomarkers.

8 Claims, 10 Drawing Sheets

(56) References Cited

OTHER PUBLICATIONS

Gaillard et al., "Photophysical studies on human retinal lipofuscin," *Photochem. Photobiol.*, 61:5 448-453 (1995).

Gaston et al., "Endogenous nitrogen oxides and bronchodilator S-nitrosothiols in human airways," *Proc. Natl. Acad. Sci. USA*, 90: 10957-10961 (1993).

Grossniklaus et al., "Clinicopathologic features of surgically excised choroidal neovascular membranes," *Ophthalmology*, 101: 1099-1111 (1994).

Grossniklaus et al., "Macrophage and retinal pigment epithelium expression of angiogenic cytokines in choroidal neovascularization," *Mol. Vis.*, 8: 119-126 (2002).

Hageman et al., "A common haplotype in the complement regulatory gene factor H (HF1/CFH) predisposes individuals to age-related macular degeneration," *Proc. Natl. Acad. Sci. USA*, 102:20 7227-7232 (2005).

Hageman et al., "An integrated hypothesis that considers drusen as biomarkers of immune-mediated processes at the RPE-Bruch's membrane interface in aging and age-related macular degeneration," *Prog. Retin. Eye Res.*, 20:6 705-732 (2001).

Hageman et al., "Molecular composition of drusen as related to substructural phenotype," *Mol. Vis.*, 5: 28 (1999).

Hageman et al., "Vitronectin is a constituent of ocular drusen and the vitronectin gene is expressed in human retinal pigmented epithelial cells," *FASEB J.*, 13: 477-484 (1999).

Haines et al., "Complement factor H variant increases the risk of age related macular degeneration," *Science*, 308: 419-421 (2005).

Hollyfield et al., "Oxidative damage-induced inflammation initiates age-related macular degeneration," *Nat. Med.*, 14: 194-198 (2008).

Ischiropoulos H., "Biological tyrosine nitration: a pathophysiological function of nitric oxide and reactive oxygen species," *Arch. Biochem. Biophys.*, 356:1 1-11 (1998).

Jha et al., "The complement system in ocular diseases," *Mol. Immunol.*, 44:16 3901-3908 (2007).

Johnson et al., "A potential role for immune complex pathogenesis in drusen formation," *Exp. Eye Res.*, 70: 441-449 (2000).

Karwatowski et al., "Preparation of Bruch's membrane and analysis of the age-related changes in the structural collagens," *Br. J. Ophthalmol.*, 79: 944-952 (1995).

Klein et al., "Prevalence of age-related maculopathy, The Beaver Dam Eye Study," *Ophthalmology*, 99: 933-943 (1992).

Klein et al., "Complement factor H polymorphism in age-related macular degeneration," *Science*, 308:5720 385-389 (2005).

Laine et al., "Y402H polymorphism of complement factor H affects binding affinity to C-reactive protein," *J. Immunol.*, 178: 3831-3836 (2007).

Lyda et al., "Studies of Bruch's membrane; flow and permeability studies in a Bruch's membrane-choroid preparation," *Am. J. Ophthalmol.*, 44: 362-369; discussion 369-370 (1957).

Marietta et al., "Macrophage oxidation of L-arginine to nitrite and nitrate: nitric oxide is an intermediate," *Biochemistry*, 27: 8706-8711 (1988).

Mitchell et al., "Prevalence of age-related maculopathy in Australia. The Blue Mountains Eye Study," *Ophthalmology*, 102: 1450-1460 (1995).

Miyagi et al., "Evidence that light modulates protein nitration in rat retina," *Mol. Cell Proteomics*, 1: 293-303 (2002).

Moore et al., "Age-related variation in the hydraulic conductivity of Bruch's membrane," *Invest. Ophthalmol. Vis. Sci.*, 36:7 1290-1297 (1995).

Mullins et al., "Drusen associated with aging and age-related macular degeneration contain proteins common to extracellular deposits associated with atherosclerosis, elastosis, amyloidosis, and dense deposit disease," *FASEB J.*, 14: 835-846 (2000).

Newsome et al., "Bruch's membrane age-related changes vary by region," *Curr. Eye Res.*, 6:10 1211-1221 (1987).

Paik et al., "The nitrite/collagen reaction: nonenzymatic nitration as a model system for age-related damage," *Connect Tissue Res.*, 42:2 111-122 (2001).

Paik et al., "The nitrite/elastin reaction: implications for in vivo degenerative effects," *Connect Tissue Res.*, 36:3 241-251 (1997).

Parish et al., "Isolation and one-step preparation of A2E and *iso*-A2E, fluorophores from human retinal pigment epithelium," *Proc. Natl. Acad. Sci. USA*, 95: 14609-14613 (1998).

Pauleikhoff et al., "Drusen as risk factors in age-related macular disease," *Am. J. Ophthalmol.*, 109: 38-43 (1990).

Rozanowska et al., "Blue light-induced singlet oxygen generation by retinal lipofuscin in non-polar media," *Free Radic. Biol. Med.*, 24:7/8 1107-1112 (1998).

Ruberti et al., "Quick-freeze/deep-etch visualization of age-related lipid accumulation in Bruch's membrane," *Invest. Ophthalmol. Vis. Sci.*, 44:4 1753-1759 (2003).

Schaumberg et al., "High-sensitivity C-reactive protein, other markers of inflammation, and the incidence of macular degeneration in women," *Arch. Ophthalmol.*, 125: 300-305 (2007).

Sellner P. A., "The movement of organic solutes between the retina and pigment epithelium," *Exp. Eye Res.*, 43:4 631-639 (1986).

Skerka et al., "Defective complement control of factor H (Y402H) and FHL-1 in age-related macular degeneration," *Mol. Immunol.*, 44: 3398-3406 (2007).

Solberg et al., "The association between cigarette smoking and ocular diseases," *Surv. Ophthalmol.*, 42:6 535-547 (1998).

Streilein J. W., "Ocular immune privilege: the eye takes a dim but practical view of immunity and inflammation," *J. Leukoc. Biol.*, 74: 179-185 (2003).

Sun et al., "Bruch's membrane aging decreases phagocytosis of outer segments by retinal pigment epithelium," *Mol. Vis.*, 13: 2310-2319 (2007).

Tang et al., "New Insights into Retinoid Metabolism and Cycling Within the Retina," *Prog. Ret. Eye Res.*, 32: 48-63 (2013).

Tezel et al., "Reengineering of aged Bruch's membrane to enhance retinal pigment epithelium repopulation," *Invest. Ophthalmol. Vis. Sci.*, 45: 3337-3348 (2004).

Wang et al., "Altered function of factor I caused by amyloid β: implication for pathogenesis of age-related macular degeneration from Drusen," *J. Immunol.*, 181: 712-720 (2008).

Wang et al., "Nitrite-modified extracellular matrix proteins deleteriously affect retinal pigment epithelial cell function and viability: a comparison study with nonenzymatic glycation mechanisms," *Curr. Eye Res.*, 30: 691-702 (2005).

Wu et al., "Oxidative stress modulates complement factor H expression in retinal pigmented epithelial cells by acetylation of FOX03," *J. Biol. Chem.*, 282: 22414-22425 (2007).

Yamamoto et al., "Scanning electron microscopic observation of Bruch's membrane with the osmium tetroxide treatment," *Br. J. Ophthalmol.*, 73: 162-167 (1989).

Yasukawa et al., "Glycoxidized particles mimic lipofuscin accumulation in aging eyes: a new age-related macular degeneration model in rabbits," *Graefes Arch. Clin. Exp. Ophthalmol.*, 245: 1475-1485 (2007).

\* cited by examiner

A2E (m/z 592)  Nitro-A2E (m/z 637)

BIOMARKERS OF INFLAMMATION IN BRUCH'S MEMBRANE OF THE HUMAN RETINA

BACKGROUND OF THE INVENTION (1) Field of the Invention

The present invention relates to diagnostic biomarkers. In particular, the present invention relates to biomarkers of aging and disease in the retina.

(2) Description of Related Art

Age-related macular degeneration (AMD) is a disease leading to severe visual loss and legal blindness in the elderly population (Klein et al. 1992; Mitchell et al. 1995). The pathophysiology of AMD is complex and can include genetic predispositions, accumulation of lipofuscin and drusen, local inflammation and neovascularization. Recently four independent research groups used different methods to screen the genomes from different groups of AMD patients. All four studies discovered a commonly inherited variant (Y402H) of the complement factor H (CFH) gene that significantly increases the risk of AMD (Edwards et al. 2005; Hageman et al. 2005; Haines et al. 2005; Klein et al. 2005). This finding links genetics and inflammation. Before this finding, the study of the components of drusen had provided compelling evidence that inflammatory and immune-mediated events participate in the development of drusen and progression of AMD. Protein components of drusen include immunoglobulins, components of the complement pathway (e.g., C5 and C5b-9), molecules involved in the acute-phase response to inflammation (e.g., Amyloid P component), and proteins that modulate the immune response (e.g., vitronectin, clusterin, and apolipoprotein E) (Hageman and Muffins 1999; Hageman et al. 1999; Johnson et al. 2000; Mullins et al. 2000). The finding that macrophages are important in choroidal neovascularization (CNV) also supports the involvement of inflammation in AMD (Grossnikiaus et al. 2002). Recent research provided further evidence that inflammation is involved in the development of AMD (Chen et al. 2007; Laine et al. 2007; Schaumberg et al. 2007; Skerka et al. 2007) and the link between inflammation, drusen and oxidative stress (Wu et al. 2007; Hollyfield et al. 2008; Wang et al. 2008).

During inflammation, large fluxes of nitric oxide (NO) are released through the activation of inducible nitric oxide synthase (Marletta et al. 1988; Carreras et al. 1994). Nitrite concentration is reported to be nearly doubled in the diabetic retina (El-Remessy et al. 2003). Cigarette smoking, which has been strongly associated with the development of AMD (Solberg et al. 1998), is also an important chronic contributor to human NO exposure (Council 1986; Borland and Higenbottam 1987). Patients with AMD have significantly higher plasma NO levels than control subjects (Evereklioglu et al. 2003). NO itself is a relatively unreactive radical, however, it is able to form other reactive intermediates including nitrite ($NO_2^-$), peroxynitrite ($ONOO^-$), $NO_2$, and $N_2O_3$, etc that can modify proteins, lipids and other compounds. Nitrite is one of the major NO metabolic products and has been used as a marker of NO production (Farrell et al. 1992; Gaston et al. 1993). In addition, nonenzymatic nitration of long lived protein such as extracellular matrix proteins is a well known pathway that has been associated with inflammation (Bailey et al. 1998; Paik et al. 2001). The extracellular matrix proteins, such as collagen and elastin have been reported to be nonenzymatically modified by nitrite at physiological pH (Paik et al. 1997; Paik et al. 2001). Applicants have shown that nitrite-modification of basement membrane-like extracellular matrix proteins can impart deleterious effects on adjacent epithelial cell function and viability (Wang et al. 2005) and impair phagocytic capacity (Sun et al. 2007).

Bruch's membrane lies between the choroidal capillary bed and retinal pigment epithelial (RPE) cells. The exchange of various materials between the underlying choriocapillaris and overlying RPE occurs through Bruch's membrane (Lyda et al. 1957; Sellner 1986). Bruch's membrane is permeable to macromolecules up to 300 kD in size in healthy eyes, but there are numerous examples of pathological processes in which larger macromolecules or even cells, including macrophages and leukocytes, can traverse Bruch's membrane in the diseased eye (Crane and Liversidge 2008). In addition to Bruch's membrane, trafficking of material from the RPE to the choriocapillaris is limited in the healthy eye by tight junctions between adjacent cells of the RPE monolayer. This outer blood-retinal barrier is part of the specialized ocular microenvironment that confers protection or immune privilege to mitigate the effect of deleterious immune responses (Streilein 2003). Nevertheless, this barrier is altered in pathological circumstances, and breakdown of the outer blood retinal barrier, including macrophage and leukocyte infiltration of the retina, are implicated in many diseases including AMD (Jha et al. 2007). Several investigators have suggested that age-related damage to Bruch's membrane allows for the accumulation of abnormal extracellular deposits, called drusen, between the basal lamina of the RPE and the inner collagen layer of Bruch's membrane (Newsome et al. 1987; Pauleikhoff et al. 1990; Mullins et al. 2000; Crabb et al. 2002). The accumulation of drusen is thought to elicit a local inflammatory response (Anderson et al. 2002; Yasukawa et al. 2007; Hollyfield et al. 2008).

Recently Applicants have shown that age-related changes in human Bruch's membrane can exert significant deleterious effects on RPE function that are independent of cell aging, including impairing the ability of cultured RPE to phagocytize photoreceptor outer segments (Sun et al. 2007). A similar effect on RPE function is observed after nonenzymatic nitration of RPE basement membrane in tissue culture (Wang et al. 2005). Surprisingly, there have been no studies that have reported nitrite modification occurring in intrinsic Bruch's membrane proteins or extrinsic deposits, although tyrosine nitration has been shown to occur in photoreceptor cells (Miyagi et al. 2002). However, previous studies have demonstrated that numerous structural and molecular alterations occur within human Bruch's membrane as a function of age. These changes, which disrupt the normal molecular architecture of Bruch's membrane, include: (1) structural changes in the main collagen frame work, including cross-linking and deposition of long-spaced collagen (Yamamoto and Yamashita 1989), (2) qualitative and quantitative changes in the native extracellular matrix molecules (Pauleikhoff et al. 2000), (3) deposition of abnormal extrinsic molecules including fluorescent products that accumulate in drusen (Ruberti et al. 2003), (4) macromolecular changes in the structure of Bruch's membrane, such as calcification, cracks or loss of inner layers due to inadequate basal membrane regeneration as in geographic atrophy (Feeney-Burns and Ellersieck 1985), (Grossniklaus et al. 1994), and (5) changes in the physical characteristic of Bruch's membrane, such as an age-dependent increase in trans-membrane hydraulic conductivity (Moore et al. 1995) and age-related linear decline in collagen solubility, an index of deleterious cross-linking (Karwatowski et al. 1995), 3-nitrotyrosine is known as a specific marker for inflammation-induced oxidative damage to proteins. In addition to proteins, Bruch's membrane also contains lipids, lipofuscin and carbohydrates (Hageman et al. 2001; Yasukawa et al.

2007). Lipofuscin is a mixture of autofluorescent material that accumulates in the RPE cells and is reported to photochemically generate a series of reactive oxygen species, including singlet oxygen, hydrogen peroxide, and superoxide anions (Gaillard et al. 1995; Rozanowska et al. 1998) that can enhance oxidative stress in the RPE. One of the major organic soluble chromophores in lipofuscin is A2E (2-[2,6-dimethyl-8-(2,6,6-trimethyl-1-cyclohexen-1-yl)-1E, 3E,5E,7E-octatetraenyl]-1-(2-hydroxyethyl)-4-[4-methyl-6-(2,6,6-trimethyl-1-cyclohexen-1-yl)-1E,3E,5E-hexatrienyl]-pyridinium).

It would be desirable to be able to identify individuals with a propensity for inflammation so that an effective treatment or preventative measures can be appropriately taken for AMD.

BRIEF SUMMARY OF THE INVENTION

The present invention provides a method of diagnosing a patient with age-related macular degeneration (AMD), by detecting biomarkers in the patient's Bruch's membrane, and diagnosing the patient with AMD.

The present invention provides for a method of detecting the presence of AMD in a patient, by detecting biomarkers in the patient's Bruch's membrane.

The present invention also provides for a method of detecting inflammation in a patient, by detecting biomarkers in the patient's Bruch's membrane.

The present invention provides for a method of determining the progression of AMD in a patient, by detecting the presence of biomarkers 3-nitrotyrosine and nitro-A2E in the patient's Bruch's membrane, quantifying the amount of the biomarkers and comparing to a standard, and determining the progression of AMD.

The present invention provides for a method of determining efficacy of a treatment for AMD in a patient, by detecting the presence of biomarkers 3-nitrotyrosine and nitro-A2E in the patient's Bruch's membrane, quantifying the amount of the biomarkers, administering a treatment for AMD, repeating the detecting and quantifying steps, and comparing the amount of biomarkers before the treatment to the amount of biomarkers after the treatment to determine the treatment's efficacy.

The present invention further provides for a method of determining the presence of AMD in an animal model, by detecting the presence of biomarkers 3-nitrotyrosine and nitro-A2E in the animal's Bruch's membrane.

The present invention further provides for a kit for detecting the presence of disease in a patient, including an assay for biomarkers 3-nitrotyrosine and nitro-A2E.

The present invention also provides for an assay including isolated biomarkers chosen from the group consisting of 3-nitrotyrosine, nitro-A2E, and combinations thereof.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
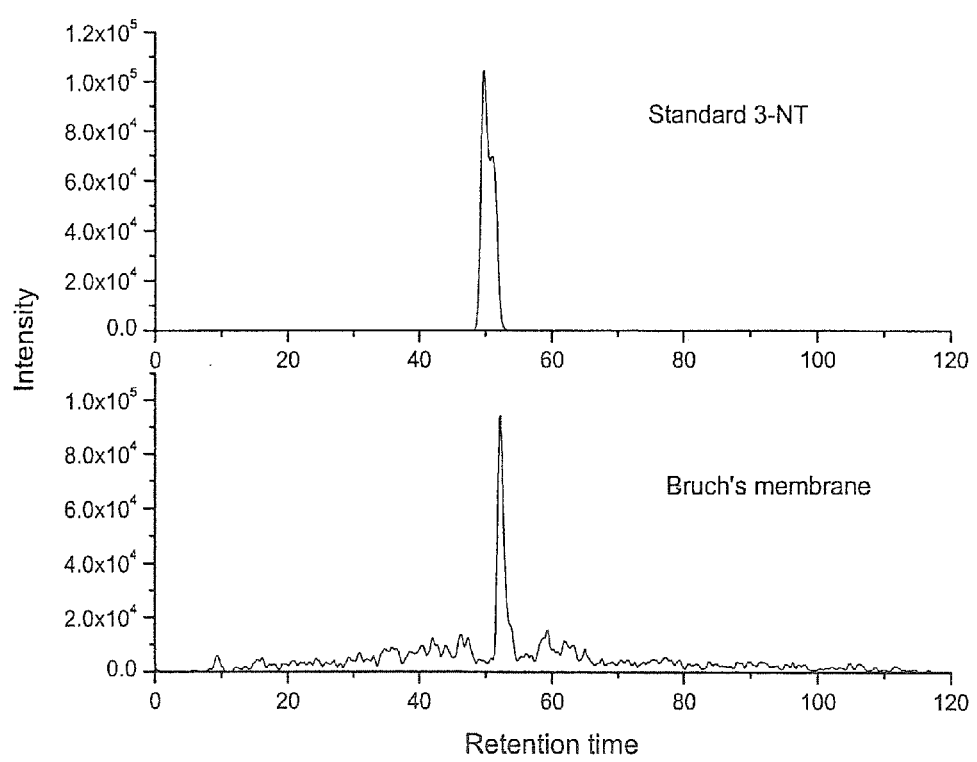
FIG. 1 is a Selected Reaction Monitoring (SRM) chromatogram of 3-NT and acid hydrolysate of BM (SRM 227.1→181.1).3-NT and acid hydrolysate of BM was analyzed by LC/MS, the SRM scan of BM acid hydrolysate has a peak with molecular mass 227 and fragment 181 and similar retention time (51 minutes) to 3-NT which indicates the presence of 3-NT in BM acid hydrolysate.

In general, the present invention provides for a method of detecting symptoms of immune-mediated processes during aging and age-related macular degeneration (AMD) by detecting the biomarkers of 3-nitrotyrosine and nitro-A2E. More specifically, the presence of 3-nitrotyrosine and nitro-A2E within human Bruch's membrane can be used to indicate inflammation and non-enzymatic nitration.

The data presented herein represents the first clear demonstration of inflammation-related chemical modifications detected in human Bruch's membrane. The Example below shows how liquid chromatography-mass spectrometry (LC-MS) was used to investigate the modifications to intrinsic and extrinsic proteins and A2E in human Bruch's membrane by reactive nitrogen species released during inflammation. Applicants have identified an increasing accumulation of 3-nitrotyrosine and nitro-A2E in human Bruch's membrane with advancing patient age.

"Biomarker", as used herein, refers to a biological molecule that is a sign of a normal or abnormal condition or disease. The biomarkers referred to herein are 3-nitrotyrosine and nitro-A2E.

Bruch's membrane is located between the endothelium layer of the choriocapillaris and a monolayer of retinal pigment epithelium (RPE). In the normal eye, Bruch's membrane serves as an attachment surface for the RPE. The outer blood-retinal barrier is formed by tight junctions between adjacent RPE; Bruch's membrane is partially responsible for limiting the movement of large molecules and cells from the choriocapillaris to the outer retina. This barrier is broken down during inflammation and inflammatory cells such as monocytes, macrophages, lymphocytes (Dua et al. 1991) and inflammatory mediators including complement components (Hollyfield et al. 2008) can traverse Bruch's membrane and accumulate within this structure. Nitric oxide released by these inflammatory cells together with the high oxygen concentration in the retina can cause oxidative stress to many components in Bruch's membrane and can lead to nonenzymatic nitration of intrinsic proteins and extrinsic products that accumulate within Bruch's membrane as a function of age. The finding of 3-nitrotyrosine and A2E nitration in Bruch's membrane as demonstrated in the Example below provides the first clear demonstration of non-enzymatic nitration of proteins and age-related deposits (A2E) within human Bruch's membrane.

Numerous changes develop within human Bruch's membrane as a function of increasing patient age, including collagen cross-linking (Yamamoto and Yamashita 1989) and the accumulation of abnormal deposits such as drusen (Ruberti et al. 2003). Physiological collagen cross-linking provides structural stability to this important structural protein, whereas nonphysiological collagen cross-linking is an imprecisely controlled process that impairs collagen structure and function (Bailey et al. 1998). Nonenzymatic collagen cross-linking can be induced by nitrite, and nitration of protein tyrosine residues to form 3-nitrotyrosine is a hallmark of tissue injury caused by inflammation. 3-nitrotyrosine has been identified in many diverse pathological conditions such as atherosclerosis, pulmonary and heart disease, viral infections, and neurological disorders (Ischiropoulos 1998). Recent studies have established that 3-nitrotyrosine serves as a "marker" of reactive nitrogen species formation and can alter protein function. For example, modification of tyrosine residues can affect the phosphorylation and dephosphorylation of tyrosine, an important mechanism of cell regulation (Di Stasi et al. 1999). Tyrosine nitration in Bruch's membrane can affect the degree of phosphorylation of some important proteins and further affect the migration of inflammatory cells through the blood retinal barrier (Erickson et al. 2007). Nitrite-induced modification of extracellular proteins can be induced in vitro (Paik et al. 1997; Paik et al. 2001), and RPE cell viability and phagocytic ability decrease on nitrite-treated extracellular matrix (Wang et al. 2005; Sun et al. 2007). Nitrite-induced changes in normal basement membrane mimic the deleterious effects of aging Bruch's membrane on RPE function. (Wang et al. 2005; Sun et al. 2007)

Figure 9:
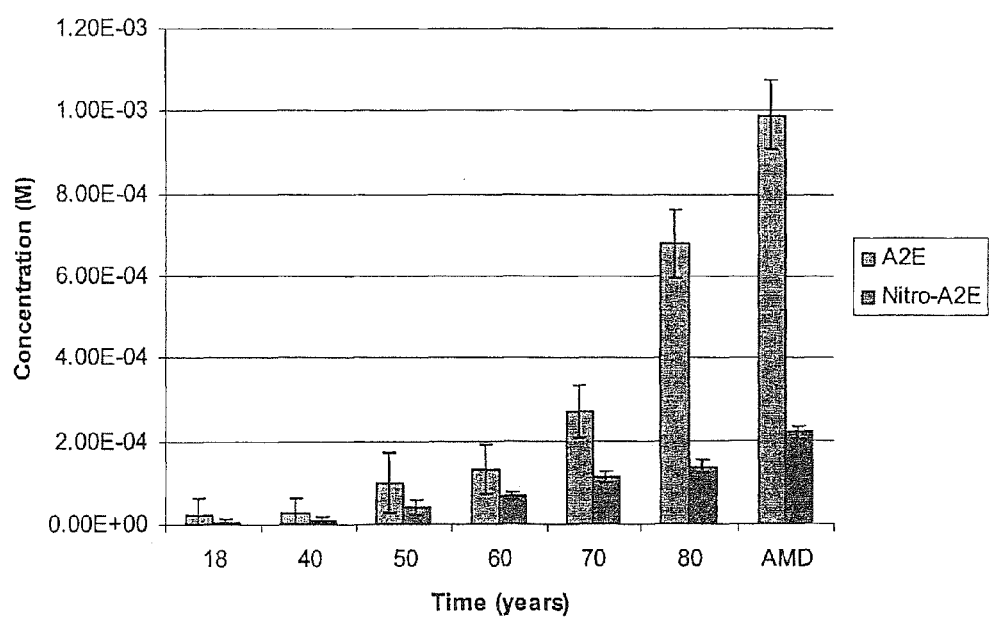
FIG. 9 shows the concentration of A2E and nitro-A2E in BM samples from >18, 40, 50, 60 70, and 80 decades of life and AMD.

Lipofuscin and other RPE cellular components have been found in drusen, the extracellular deposits located between the basal lamina of the RPE and the inner collagenous layer of the Bruch's membrane (Hageman et al. 2001; Crabb et al. 2002). One of the major components of lipofuscin is A2E, and this study demonstrates the presence of A2E in human Bruch's membrane. A2E is not normally a component of Bruch's membrane in young eyes, and significant levels of A2E or nitro A2E were not identified in samples obtained from patients in the second decade of life (FIG. 9). In addition the concentration of A2E clearly increases with patient age (FIG. 9), thus demonstrating that A2E deposition is a non-physiological process that does not occur, or occurs to a very limited extent, in young individuals. The mechanism for A2E accumulation is not known. It is believed that RPE ordinarily does not extrude or exocytose active lysosomes or lysosomal enzymes although aged RPE extrude cytoplasm with active lysosomes into Bruch's membrane (Feeney-Burns et al. 1987). It could not be determined if the A2E identified in Bruch's membrane is part of this normal extrusion process. Lipofuscin and other cellular debris accumulated in Bruch's membrane can contribute to the decreasing hydraulic conductivity observed with age (Moore et al. 1995) and also may stimulate chronic inflammation.

Figure 8:
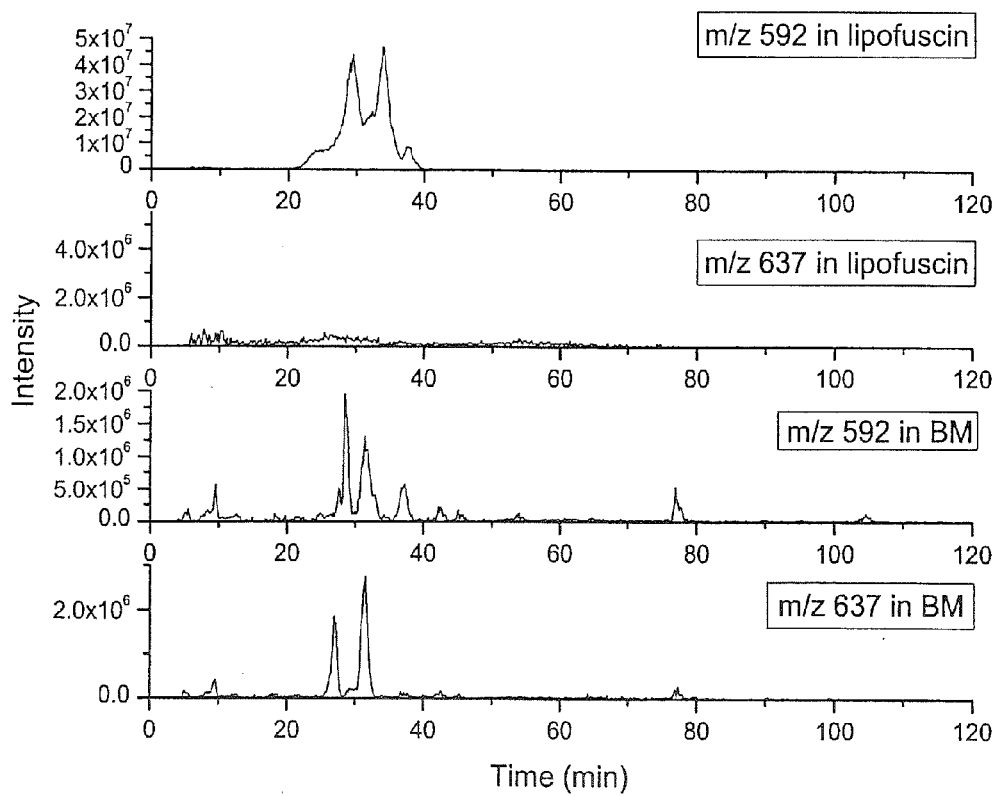
FIG. 8 is the selected ion chromatograms for A2E (m/z 592) and nitro-A2E (m/z 637) from RPE lipofuscin and BM extracts from human donor globes that were 65 yrs and older, note that nitro A2E and A2E from the BM have similar concentrations, whereas no nitro-A2E could be detected from the RPE despite increasing the sensitivity of the detector.

The results in the Example below demonstrate that 3-nitrotyrosine is present within proteins that are present within human Bruch's membrane that is isolated using previously described techniques. Previous studies using scanning and transmission electron microscopy of Bruch's membrane preparations demonstrate that the Bruch's membrane isolated in these preparations contains all 5 layers of Bruch's membrane (i.e., basal lamina of the RPE, inner collagen layer, elastin, outer collagen layer, and basal lamina of the choriocapillaris). Scanning electron microscopy demonstrates the preparation contains extracellular deposits on both the inner and the outer aspects of the RPE basal lamina (Del Priore and Tezel 1998; Tezel et al. 2004). The preparation contains intrinsic Bruch's membrane proteins as well as extracellular deposits, and therefore the 3-nitrotyrosine detected does represent modifications of intrinsic Bruch's membrane proteins, proteins located in extracellular deposits such as drusen, or both. However, it should be noted that nitro-A2E is present within the Bruch's membrane preparation but nitro-A2E was not detected in lipofuscin extracted from human RPE (FIG. 8). This shows that nitration of A2E occurs after A2E has accumulated within Bruch's membrane. Thus, non-enzymatic nitration of A2E must occur within Bruch's membrane, possibly due to nitric oxide and/or related nitrating agents such as peroxynitrite. It is likely that non-enzymatic nitration of both intrinsic Bruch's membrane proteins and extracellular deposits occur by a similar mechanism.

Therefore, in general, the present invention provides for a method of diagnosing a patient with AMD by detecting biomarkers in the patient's Bruch's membrane, and diagnosing the patient with AMD. The biomarkers can be detected with standard diagnostic techniques, such as, but not limited to a fluorescence test using a scanning laser ophthalmoscope. This is a non-invasive method performed with a common diagnostic instrument available to ophthalmologists. Fluorescent patterns obtained from the eyes of a patient with AMD having the biomarkers is different than from a healthy patient. Therefore, based on the fluorescence test, the patient can be diagnosed properly. The fluorescence test can also be used to determine the progress of treatment of AMD due to the administration of various therapies. In other words, the fluorescent pattern changes based on working therapies. In another method of detection, a sample can be taken from the patient's body, such as blood, and an assay can be performed in order to determine the presence of the biomarkers.

The biomarkers that are detected are 3-nitrotyrosine and nitro-A2E. Either one of these biomarkers can be detected, or both can be detected. Once the biomarkers are detected in a patient and a diagnosis is made, proper treatment can be sought. Through the use of the biomarkers of the present invention, detection of AMD and other diseases can be made earlier, allowing a patient to seek treatment as soon as possible.

The present invention also provides generally for a method of detecting the presence of AMD in a patient by detecting biomarkers in the patient's Bruch's membrane, i.e. by detecting 3-nitrotyrosine and nitro-A2E. The biomarkers can be detected as described above by fluorescence, or any other suitable method such as resonance raman.

The present invention provides for a method of detecting inflammation in a patient by detecting biomarkers in the patient's Bruch's membrane. The biomarkers detected are 3-nitrotyrosine and nitro-A2E, either alone or in combination, and can be detected as described above by fluorescence or any other suitable method. These biomarkers are indicators of inflammation, and once detected, the patient can be provided appropriate treatment to reduce or obviate the inflammation. Detecting inflammation can also prompt the patient to have further testing performed in order to determine the cause of the inflammation. A positive detection of inflammation can indicate the presence of diseases such as cirrhosis, arteriosclerosis, or Alzheimer's disease as well as AMD. Therefore, by detecting the biomarkers, a patient can be diagnosed with these diseases.

The present invention provides for a method of determining the progression of AMD in a patient, including the steps of detecting the presence of biomarkers 3-nitrotyrosine and nitro-A2E, either alone or in combination, in the patient's Bruch's membrane, quantifying the amount of the biomarkers and comparing to a standard, and determining the progression of AMD. The biomarkers can be detected as described above by fluorescence, or any other suitable method. The amount of 3-nitrotyrosine and nitro-A2E correlate to the progression of AMD, as shown in the Example below. Standards can be created for each stage in the progression of the disease as appropriate. In other words, the greater amounts of biomarkers detected, the later the stage of AMD, and the lesser amounts of biomarkers detected, the earlier the progression of AMD. This can be useful in determining an appropriate treatment for a patient, as some treatments can be more advantageous at different stages of the progression of the disease.

The present invention also provides for a method of determining efficacy of a treatment for AMD in a patient, including the steps of detecting the presence of biomarkers 3-nitrotyrosine and nitro-A2E in the patient's Bruch's membrane, quantifying the amount of the biomarkers, administering a treatment for AMD, repeating the detecting and quantifying steps, and comparing the amount of biomarkers before the treatment to the amount of biomarkers after the treatment to determine the treatment's efficacy. The detecting and quantifying steps have been described above. Any appropriate treatment can be administered to the patient in order to determine its efficacy. It is advantageous to perform this method so that a particular treatment can be further proscribed or changed according to the needs of the patient.

The biomarkers of the present invention can further be used in certain animal models of AMD, e.g. primates. The amount of nitro-A2E and 3-nitrotyrosine can be determined chromatographically after sacrifice, as chromatography allows mixtures of substances to be physically separated into pure components. In this method, the presence and stage of AMD can be determined as described above, as well as the efficacy of any treatment being tested on the animals. In other words, efficacy of the treatment can be determined by comparing the amount of biomarkers to a standard or also to measurements of the biomarkers taken at an earlier point in treatment.

The present invention can further include a kit for detecting the presence of AMD or other disease in a patient, and can include an assay for detecting the biomarkers 3-nitrotyrosine and nitro-A2E. For example, a blood test can be included to measure plasma levels of 3-nitrotyrosine and nitro-A2E. In this assay, appropriate antibodies are also included as well as supplies for taking a sample from the patient. In another assay, fluorescence data pertaining to the biomarkers is included for non-invasive detection using a scanning laser ophthalmoscope in order to detect particular fluorescent patterns as described above.

The present invention also provides for an assay that includes the isolated biomarkers, 3-nitrotyrosine and nitro-A2E, either alone or in combination. The assay can be used as above.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLE 1

Materials and Methods

Reagents

All-trans-retinal was purchased from A.G. Scientific, Inc. (San Diego, Calif.). Sodium nitrite, ammonium acetate, acetic acid, constant boiling hydrochloric acid and 3-nitro-L-tyrosine were purchased from Sigma-Aldrich Chemical Inc. (St. Louis, Mo.). Formic acid, trifluoroacetic acid, and ethanolamine were purchased from ACROS Organics (New Jersey, USA). Sequencing-grade modified trypsin was purchased from Promega (Madison, Wis.). All organic solvents were HPLC grade and bought from Fisher Scientific Co. (Fair Lawn, N.J.).

Bruch's Membrane Preparation

Donor human eyes were purchased from Chicago Eye Bank (Midwest Eye Banks and Transplantation Centers). Bruch's membrane tissues from different decades including >18, 40s, 50s, 60s, 70s, 80s, and from four pairs of globes (donor ages 92, 81, 83, and 79) with clinically diagnosed nonexudative AMD patients were used in this study. The preparation of Bruch's membrane followed the method described by Karwatowski et al. (Karwatowski et al. 1995).

Acid Hydrolysis

Bruch's membranes from different decades of life were pooled into three samples including <25 yrs, 40-60 yrs, and >65 yrs. These samples were dissected and prepared as previously described and then hydrolyzed in 6 M HCl at 110° C. for 24 hours using homemade glass tubes with Teflon-lined screw caps. Before hydrolysis, deoxygenation of the samples was achieved by six freeze-pump-thaw cycles. After samples were placed in the tubes, air was removed by applying a vacuum for approximately 5 minutes. After hydrolysis, excess acid was evaporated using argon gas. The samples were then resuspended in 50 mL $H_2O$ and spiked with 50 µL of 100 µM 3-Nitrotyrosine. The samples were then analyzed by LC-MS and the concentration was calculated using standard addition.

Preparation of Organic Soluble Materials from Bruch's Membrane

Isolated Bruch's membrane was cut into small pieces and placed in a homogenizer. An equal amount of $CHCl_3$:$CH_3OH$:$H_2O$ was added and gently homogenized to extract organic soluble components. The homogenized Bruch's membrane solid and supernatant were filtered through a plug of glass wool in a Pasteur pipette and separated from each other. The organic part of the extract was separated from water soluble part. The organic layer was centrifuged for 15 minutes at a speed of 5000 rpm. The supernatant from the centrifuged solution was collected. The solvent was evaporated under argon. Roughly 50 µL of methanol was added into dried extract and 20 µL of the extract solution was injected and analyzed by Liquid chromatography-mass spectrometry (LC-MS).

A2E Synthesis

A2E was synthesized as described by Parish et al. (Parish et al. 1998) with modification to the purification methods. Two equivalents of all-trans-retinal and one equivalent of ethanolamine were mixed together in ethanol with one equivalent of acetic acid. The mixture was placed in the dark at room temperature (20-25° C.) for 3-4 days. The solvent was evaporated with argon gas, and A2E was separated from the reaction mixture by HPLC with separation column (Synergi 4 μm Hydro-RP 80A 250×10.00 mm). Isocratic gradient of 3% of $H_2O$ (0.1% formic acid) and 97% methanol was applied for the separation. The reaction mixture (100 μL) was injected for 60 minutes with a flow rate of 1.0 mL/min. The retention time of A2E and iso-A2E was approximately 23 minutes. The absorption spectrum was monitored at 430 nm. A2E was verified with an ultraviolet-visible absorption spectrophotometer and mass spectrometry.

Nitro-A2E Synthesis

All procedures were performed in the dark. A2E was purified by HPLC and the solvent was evaporated as described in A2E synthesis. The concentration of A2E was determined by monitoring the absorption at 439 nm using an extinction coefficient of 36,900 L/mol cm. The concentration of A2E was determined to be 43 mM in 5 ml methanol. The solvent was then evaporated and the A2E was re-dissolved in 0.5 mL of methanol and placed into a 5 mL round bottom flask. Ammonium acetate buffer (1 mL of 0.25 M pH 5.4) and $NaNO_2$ (0.5 mL of 200 mM) were slowly added to the A2E solution. The solution was stirred with a magnetic bar and placed in the dark for 4 days. To desalt nitro-A2E, the reaction mixture was loaded on C18 Zip-Tip tips (Varian, Palo Alto, Calif.) that were prewashed with methanol and equilibrated by 0.1% TFA in water. Zip-Tip tips were washed by $H_2O$ (0.1% TFA) and samples were then eluted by methanol. The synthesized nitro-A2E was dissolved in approximately 30 μL of methanol and 20 μL of that solution was analyzed by LC-ESI-MS/MS.

High-performance Liquid Chromatography-mass Spectrometry (LC-MS) with Electrospray Ionization (ESI)

The following conditions were utilized for the analysis of the acid hydrolysate of Bruch's membrane protein. For the LC, a 150'4.6 mm Synergi Max-RP C12 column was used with a gradient of 1-10% acetonitrile (ACN) for 50 minutes, 10-60% ACN for 30 minutes, 60-100% ACN for 20 minutes and a flow rate 0.2 ml/minutes. The conditions for mass spectrometry (Thermo Finnigan LCQ Advantage and Surveyor LC system, San Jose, Calif.) were: positive polarity, capillary temperature of 200° C., source voltage of 4.5 kV, capillary voltage of 43 V, and tube lens offset of 50 V, mass-to-charge ratio, m/z, range: 200-1,000, normalized collision energy of 25%.

For the organic soluble extract of Bruch's membrane, the separation was carried out on a 150'4.6 mm Synergi Max-RP C12 column using a linear gradient of 85% to 96% methanol for 60 minutes and 96%-100% methanol for 10 minutes with a balance of water containing 0.1% TFA and a flow rate of 0.3 mL/min. For synthesized nitro-A2E analysis, the separation was carried out on a 150'4.6 mm Synergi Max-RP C12 column using an isocratic mobile phase of 5% methanol for 10 minutes and linear gradient of 5-100% methanol for 30 minutes balanced with water with 0.1% formic acid and a flow rate of 0.3 ml/min (monitored at 430 nm, 350 nm, and 250 nm). The compounds with m/z values of 592, 637, 653 and 682 were selected for subsequent MS/MS scan using normalized collision energy of 52%. These are the molecular weights of A2E and nitrated A2E. The mass spectrometer settings were source voltage 4 kV, capillary voltage 3.3 V, capillary temperature 200° C. and tube lens voltage 25 V.

Statistical Analysis

Multiple runs of each sample were analyzed and the standard deviation for each sample was calculated. A standard t-test was then used for all statistical analysis with a p<0.05 indicating that the difference between groups was statistically significant. In addition, ANOVA one-way statistical analysis with a 95% confidence level was performed on the Bruch's membrane samples from different decades of life.

Results

Identification of Tyrosine Nitration in Bruch's Membrane

Figure 2:
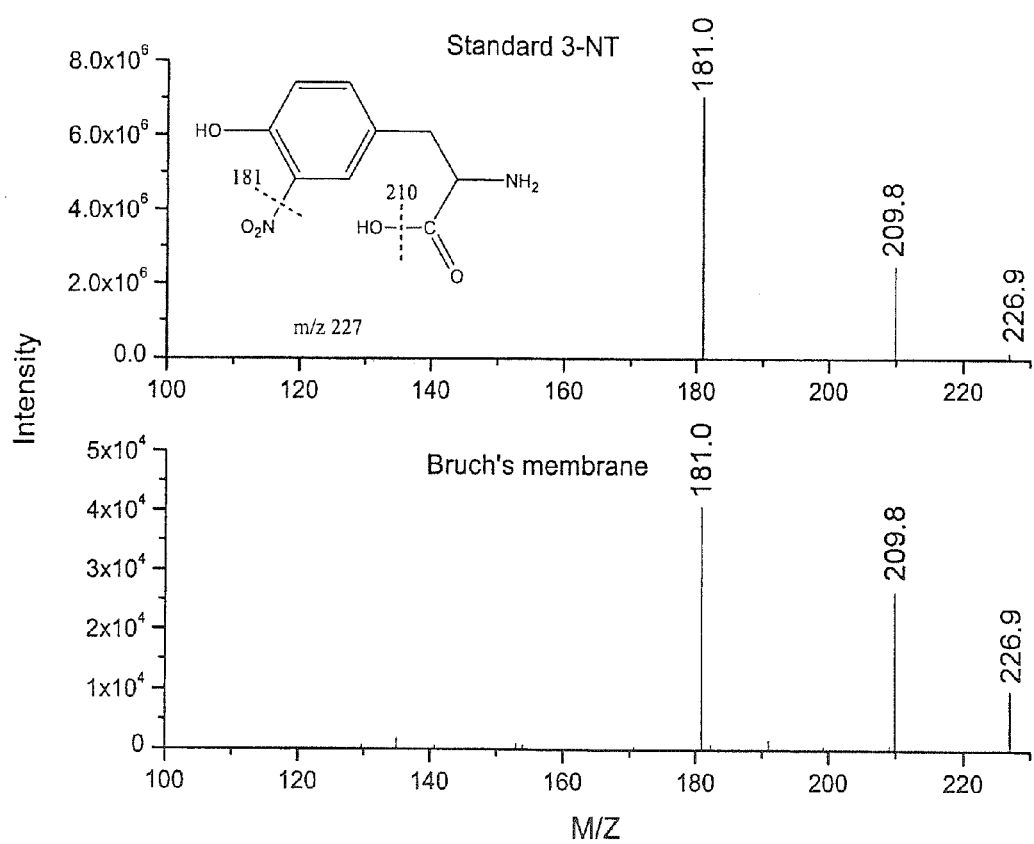
FIG. 2 is a tandem mass spectra of standard 3-nitrotyrosine and component with m/z 227.0 at RT 51 mins in BM, the tandem mass spectrum of the component at RT 51 minutes from human BM extracted from 72-75 year old donors is very similar to the tandem mass spectrum of 3-NT, and the inset gives the predicted fragmentation of 3-NT.
Figure 3:
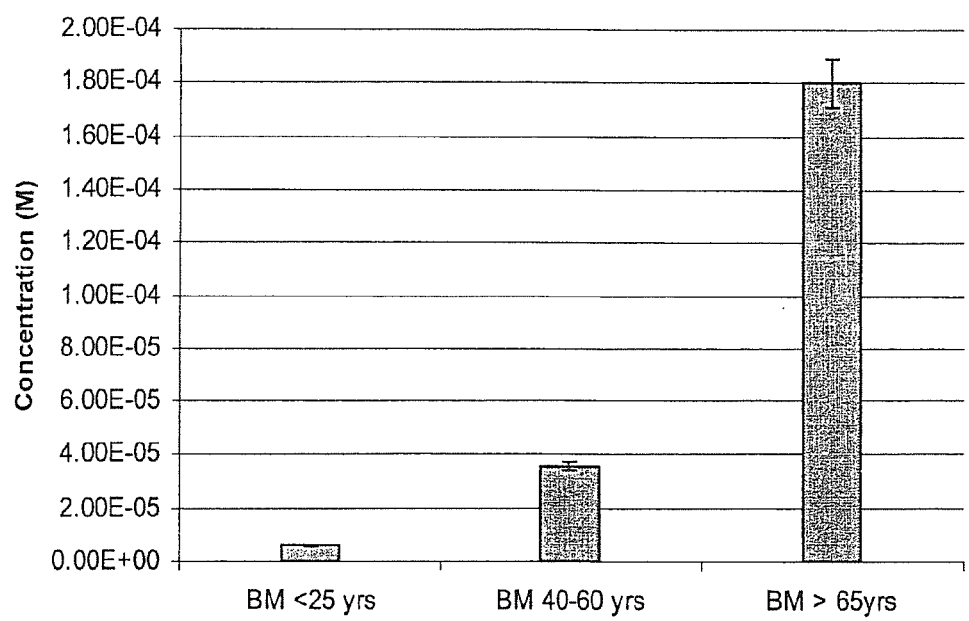
FIG. 3 is a graph of the concentration of 3-nitrotyrosine in BM samples from <25, 40-60, and >65 years.

To determine if tyrosine nitration occurs in Bruch's membrane, Bruch's membrane was acid hydrolyzed and analyzed by LC-MS. 3-nitrotyrosine (3-NT), which is an important biomarker of nonenzymatic nitration, is stable under acid hydrolysis (Crowley et al. 1998). The m/z of the quasimolecular ion ($[MH]^+$) of 3-nitrotyrosine is 227.0. This molecule easily loses a nitro group under collision-induced dissociation (CID) forming a fragment with m/z 181.0. Therefore, selective reaction monitoring (SRM) was used (parent ion m/z=227.0 with daughter ion m/z=181.0) to specifically monitor the presence of 3-nitrotyrosine. FIG. 1 gives the results of selective reaction monitoring scans of the acid hydrolysate of Bruch's membrane and standard 3-nitrotyrosine. The SRM scan of acid hydrolysate of Bruch's membrane has a peak with similar retention time to the peak of 3-nitrotyrosine. The tandem mass spectrum of the compound in this peak is also similar to the tandem mass spectrum of 3-nitrotyrosine (FIG. 2). Identical experiments were performed on three samples of human Bruch's membranes from different donors to determined the relative concentration of 3-nitrotyrosine within the human Bruch's membrane samples as a function of patient age. Approximately 6 pieces of Bruch's membrane from 4 different donors from each decade (including <25 yrs, 40-60 yrs, and >65 yrs), were obtained. These samples were then extracted as previously described in Materials and Methods. To quantify the actual concentration of 3-nitrotyrosine, the standard addition of 50 μM solution of 3-nitrotyrosine was added to each of the samples before analysis with LC-MS. FIG. 3 displays the concentrations of 3-nitrotyrosine in the different decades. The presence of 3-nitrotyrosine is negligible in the <25 yrs sample of BM. There was a small increase in the BM sample between the ages of 40 to 60 yrs followed by a substantial increase in the BM sample >65 yrs. The exponential increase of 3-nitrotyrosine in BM, observed in FIG. 3, suggests that tyrosine nitration occurs in human Bruch's membrane as a function of age, which may be related to the inflammatory response.

Identification of Nitro-A2E in Bruch's Membrane

Figures 4A, 4B:
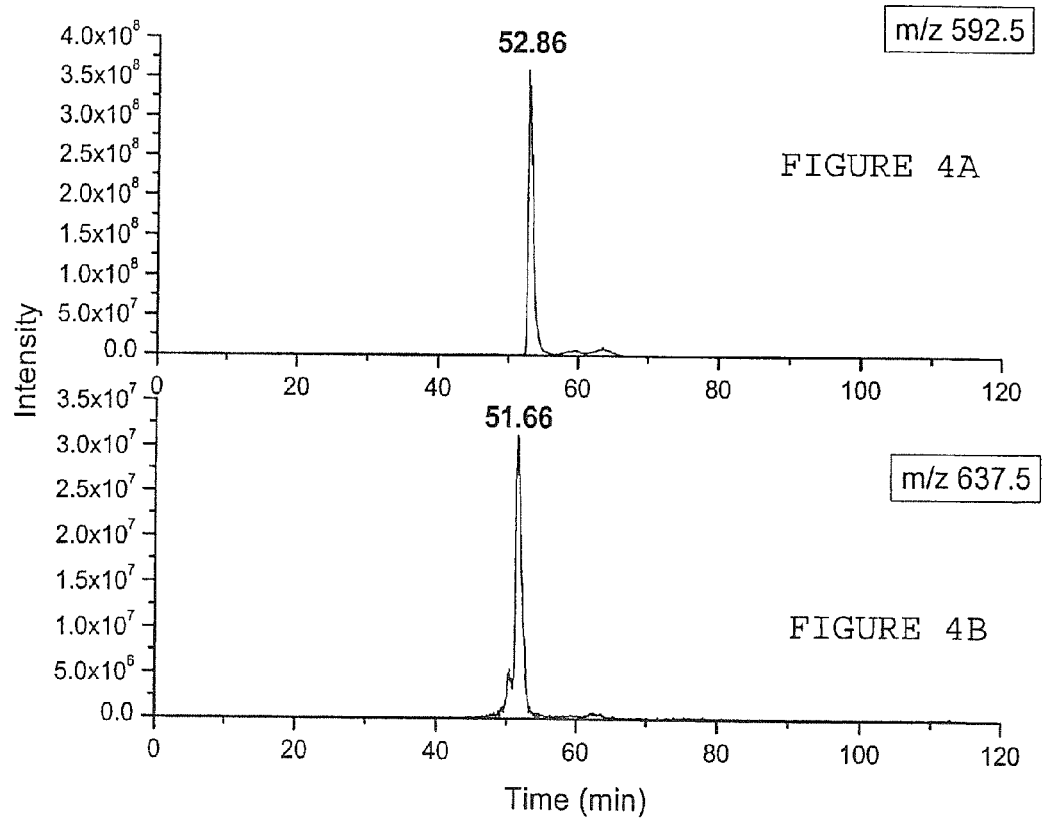
FIGS. 4A and 4B are selected ion chromatograms for synthetic A2E (4A) and nitro-A2E (4B), since nitro-A2E is slightly more polar than A2E, its RT is somewhat shorter.
Figure 5A:
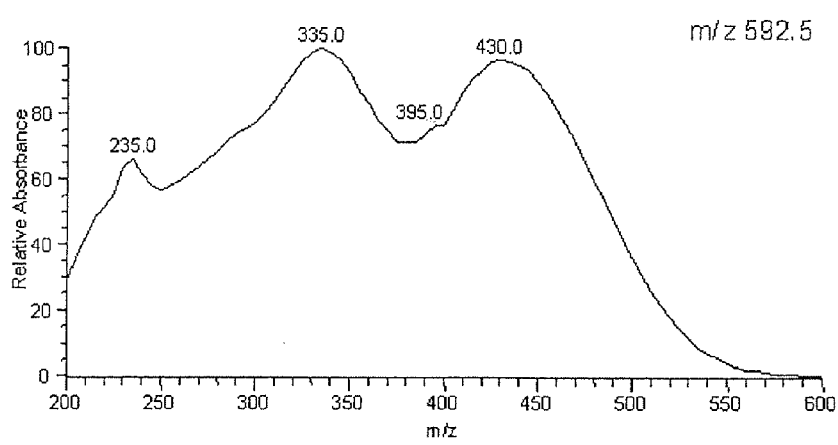
FIGS. 5A and 5B show the UV spectra for A2E (m/z 592.5) and for nitro-A2E (m/z 637.5), respectively.
Figure 5B:
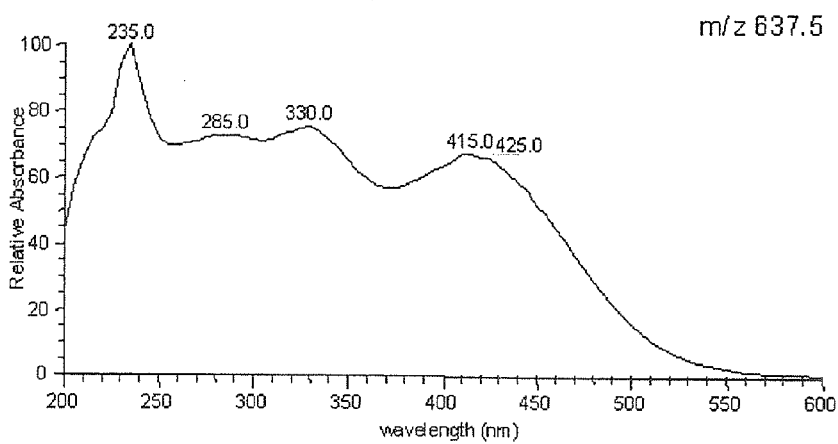

To investigate the hypothesis that one of the major components in lipofuscin, A2E, can be modified by reactive nitrogen species resulting in the formation of nitro-A2E, nitro-A2E was synthesized as described in Materials and Methods and then analyzed by mass spectrometry. To confirm the presence of A2E and nitro-A2E, the total ion chromatogram for synthetic nitro-A2E filtered for m/z 592.5 and 637.5 are displayed in FIG. 4 with corresponding retention times. The ultraviolet-visible absorption spectra of m/z 592.5 (A2E) and 637.5 (nitro-A2E) were also compared (FIGS. 5A and 5B). A2E had absorption peaks at 335 and 430 nm, which corresponds to previously reported results (Parish et al. 1998). The absorption spectrum of nitro-A2E (FIG. 5B) is very similar to the absorption spectrum observed in FIG. 5A for A2E. However, the two most intense absorption peaks were located at 330 and 415 nm, indicating that nonenzymatic nitration induces an expected slight blue shift in the absorption spectrum.

Figure 6:
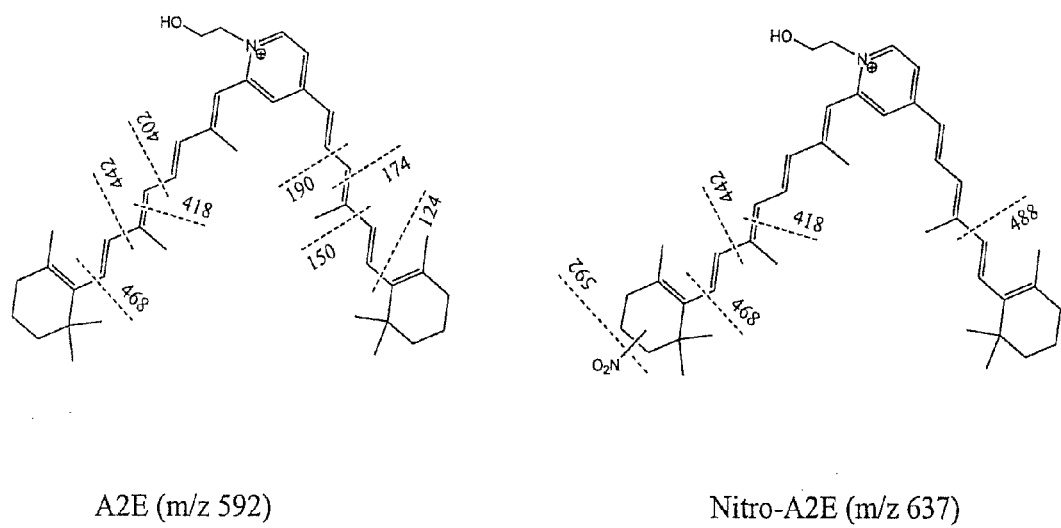
FIG. 6 is a depiction of structures of A2E (m/z 592) and nitro-A2E (m/z 637) showing characteristic cleavage points and the resulting fragment molecular weights.
Figure 7A:
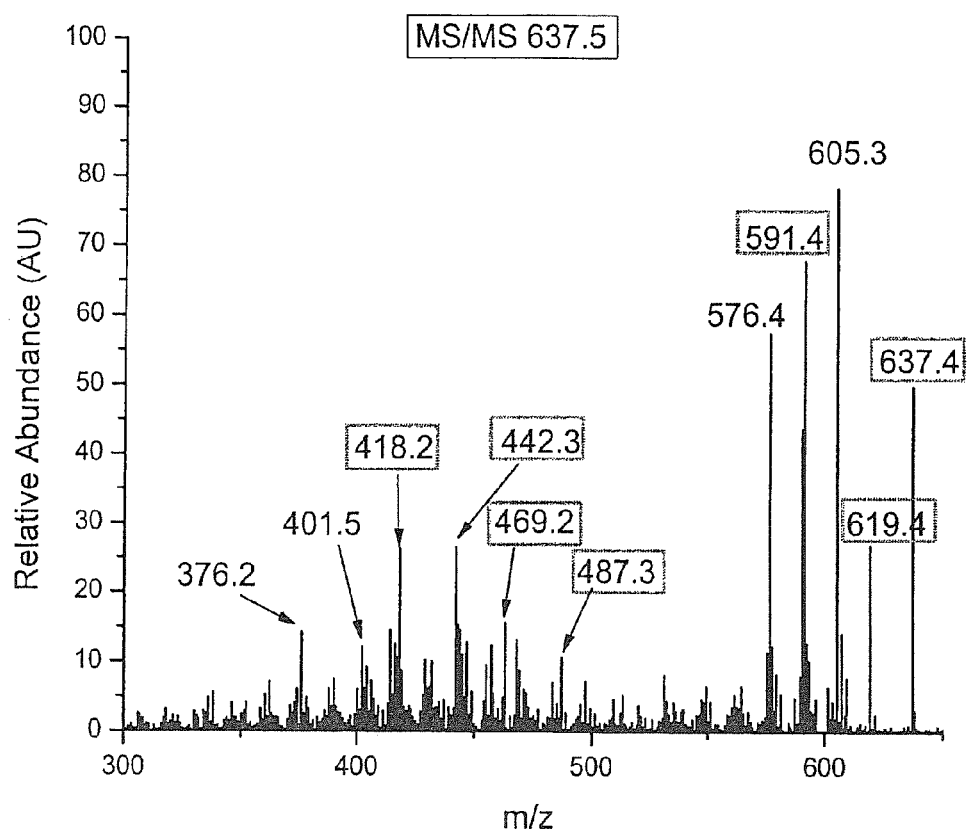
FIG. 7A shows the tandem mass spectrum of synthetic nitro-A2E.

The structure of A2E is compared to the predicted structure of nitro-A2E in FIG. 6 with characteristic cleavages identified (Dillon et al. 2004). The m/z of synthetic nitro-A2E measured by mass spectrometry is 637.5, which is in agreement with this predicted structure. FIG. 7A displays the tandem mass spectrum of synthetic nitro-A2E. The major fragments from the CID spectrum match the predicted structure and characteristic fragmentations shown in FIG. 6.

Figure 7B:
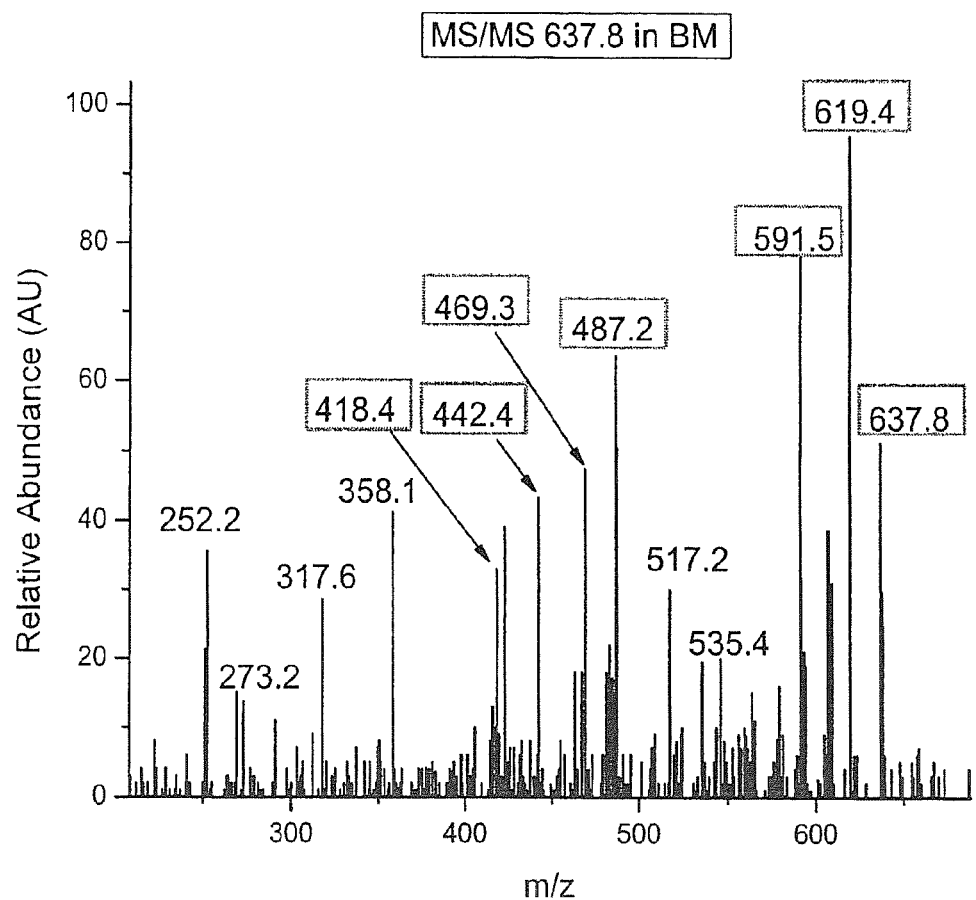
FIG. 7B shows the tandem mass spectrum of nitro-A2E isolated from 65 yrs and older BM (Box=mass same in synthetic nitro-A2E and nitro-A2E isolated from 65 yrs and older BM)

To investigate the possible presence of nitro-A2E in vivo, the organic soluble components in Bruch's membrane from 70 yr old donor globes were extracted and analyzed by LC/MS. The total ion chromatogram revealed a peak with m/z 592, which was identified as A2E based on its absorption spectrum and characteristic fragmentation pattern. A peak with m/z 637.5 within the total ion chromatogram was also seen at approximately the same retention time as the peak with m/z 637.5 located in the synthetic nitro-A2E sample, suggesting the presence of nitro-A2E within the Bruch's membrane sample. This peak was then fragmented by collision-induced dissociation to confirm the identification of nitro-A2E. FIG. 7B displays the tandem mass spectrum of the component with m/z 637.5 located within the Bruch's membrane extract. The major fragments correspond to characteristic cleavages illustrated in FIG. 6 and also observed in the authentic nitro-A2E sample (FIG. 7A). The total ion chromatogram also contained samples with molecular weights of m/z 653 and 682, which suggests the presence of oxidized-nitrated A2E and doubly nitrated A2E, but the amounts were insufficient to acquire a full CID spectrum. However, in a preliminary experiment, the presence of these peaks was absent from Bruch's membrane extracts from two 18 yr old donor globes (data not shown).

It was next determined whether A2E was nitrated within RPE lipofuscin and then transported to Bruch's membrane, or whether nitration of A2E occurred after A2E accumulation within Bruch's membrane. To address this issue approximately ten samples of the organic soluble extract of lipofuscin and the organic soluble extract of Bruch's membrane from three donors were analyzed by LC-MS and compared. FIG. 8 displays filtered total ion chromatograms for A2E (m/z 592) and nitro-A2E (m/z 637) in RPE lipofuscin and Bruch's membrane. The presence of several peaks in the chromatograms result from several isomers co-existing (Parish et al. 1998). The highest concentration of A2E was observed in RPE lipofuscin followed by a significantly lower concentration (30-40 fold) within Bruch's membrane extract. Nitro-A2E was absent from the lipofuscin samples tested but nitro-A2E was detected within human Bruch's membrane, thus providing strong evidence that the nitration of A2E is specific to Bruch's membrane and does not occur within RPE lipofuscin.

Concentration of Nitro-A2E in Bruch's Membrane Samples from Different Decades of Life The relative concentration of A2E was then determined within the human Bruch's membrane samples as a function of patient age. Approximately 8 pieces of Bruch's membrane from 4 different donors from each decade (including >20s, 40s, 50s, 60s, 70s, 80s), and clinically diagnosed nonexudative AMD were obtained. These samples were then extracted as previously described in Materials and Methods. To quantify the actual concentration of A2E and nitro-A2E, an internal standard of 50 µM tryptophan was added to each of the samples before analysis with LC-MS. FIG. 9 displays the concentrations of A2E and nitro-A2E throughout the different decades. The accumulation of both A2E and nitro-A2E is negligible up to the $4^{th}$ decade of life. However, between the $4^{th}$ and $5^{th}$ decades there is a substantial increase in the concentrations of both A2E and nitro-A2E, which continues to rise throughout the $6^{th}$, $7^{th}$ and $8^{th}$ decades. To determine if these results were relevant to AMD, the concentrations of A2E and nitro-A2E throughout the different decades were also compared to the concentrations found in nonexudative AMD as shown in FIG. 9. The nonexudative AMD samples had the highest concentration of A2E and nitro-A2E. Patients in the $8^{th}$ decade of life displayed similar concentration of both the A2E and nitro-A2E as seen in the nonexudative AMD samples.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Anderson D H, Mullins R F, Hageman G S, Johnson L V (2002) A role for local inflammation in the formation of drusen in the aging eye. Am J Ophthalmol 134: 411-431

Bailey A J, Paul R G, Knott L (1998) Mechanisms of maturation and ageing of collagen. Mech Ageing Dev 106: 1-56

Borland C, Higenbottam T (1987) Nitric oxide yields of contemporary UK, US and French cigarettes. Int J Epidemiol 16: 31-34

Carreras M C, Pargament G A, Catz S D, Poderoso J J, Boveris A (1994) Kinetics of nitric oxide and hydrogen peroxide production and formation of peroxynitrite during the respiratory burst of human neutrophils. FEBS Lett 341: 65-68

Chen M, Forrester J V, Xu H (2007) Synthesis of complement factor H by retinal pigment epithelial cells is down-regulated by oxidized photoreceptor outer segments. Exp Eye Res 84: 635-645

Council N R (1986) Environmental Tobacco Smoke: Measuring Exposure and Assessing Health Effects. National Academy Press, Washington D.C.

Crabb J W, Miyagi M, Gu X, Shadrach K, West K A, Sakaguchi H, Kamei M, Hasan A, Yan L, Rayborn M E, Salomon R G, Hollyfield J G (2002) Drusen proteome analysis: an approach to the etiology of age-related macular degeneration. Proc Natl Acad Sci USA 99: 14682-14687

Crane I J, Liversidge J (2008) Mechanisms of leukocyte migration across the blood-retina barrier. Semin Immunopathol 30: 165-177

Crowley J R, Yarasheski K, Leeuwenburgh C, Turk J, Heinecke J W (1998) Isotope dilution mass spectrometric quantification of 3-nitrotyrosine in proteins and tissues is facilitated by reduction to 3-aminotyrosine. Anal Biochem 259: 127-135

Del Priore L V, Tezel T H (1998) Reattachment rate of human retinal pigment epithelium to layers of human Bruch's membrane. Arch Ophthalmol 116: 335-341

Di Stasi A M, Mallozzi C, Macchia G, Petrucci T C, Minetti M (1999) Peroxynitrite induces tryosine nitration and modulates tyrosine phosphorylation of synaptic proteins. J Neurochem 73: 727-735

Dillon J, Wang Z, Avalle L B, Gaillard E R (2004) The photochemical oxidation of A2E results in the formation of a 5,8,5',8'-bis-furanoid oxide. Exp Eye Res 79: 537-542

Dua H S, McKinnon A, McMenamin P G, Forrester J V (1991) Ultrastructural pathology of the 'barrier sites' in experimental autoimmune uveitis and experimental autoimmune pinealitis. Br J Ophthalmol 75: 391-397

Edwards A O, Ritter R, 3rd, Abel K J, Manning A, Panhuysen C, Farrer L A (2005) Complement factor H polymorphism and age-related macular degeneration. Science 308: 421-424

El-Remessy A B, Behzadian M A, Abou-Mohamed G, Franklin T, Caldwell R W, Caldwell R B (2003) Experimental diabetes causes breakdown of the blood-retina barrier by a mechanism involving tyrosine nitration and increases in expression of vascular endothelial growth factor and urokinase plasminogen activator receptor. Am J Pathol 162: 1995-2004

Erickson K K, Sundstrom J M, Antonetti D A (2007) Vascular permeability in ocular disease and the role of tight junctions. Angiogenesis 10: 103-117

Evereklioglu C, Er H, Doganay S, Cekmen M, Turkoz Y, Otlu B, Ozerol E (2003) Nitric oxide and lipid peroxidation are increased and associated with decreased antioxidant enzyme activities in patients with age-related macular degeneration. Doc Ophthalmol 106: 129-136

Farrell A J, Blake D R, Palmer R M, Moncada S (1992) Increased concentrations of nitrite in synovial fluid and serum samples suggest increased nitric oxide synthesis in rheumatic diseases. Ann Rheum Dis 51: 1219-1222

Feeney-Burns L, Ellersieck M R (1985) Age-related changes in the ultrastructure of Bruch's membrane. Am J Ophthalmol 100: 686-697.

Feeney-Burns L, Gao C L, Tidwell M (1987) Lysosomal enzyme cytochemistry of human RPE, Bruch's membrane and drusen. Invest Ophthalmol V is Sci 28: 1138-1147

Gaillard E R, Atherton S J, Eldred G, Dillon J (1995) Photophysical studies on human retinal lipofuscin. Photochem Photobiol 61: 448-453

Gaston B, Reilly J, Drazen J M, Fackler J, Ramdev P, Arnelle D, Mullins M E, Sugarbaker D J, Chee C, Singel D J, et al. (1993) Endogenous nitrogen oxides and bronchodilator S-nitrosothiols in human airways. Proc Natl Acad Sci USA 90: 10957-10961

Grossniklaus H E, Hutchinson A K, Capone A, Jr., Woolfson J, Lambert H M (1994) Clinicopathologic features of surgically excised choroidal neovascular membranes. Ophthalmology 101: 1099-1111.

Grossniklaus H E, Ling J X, Wallace T M, Dithmar S, Lawson D H, Cohen C, Elner V M, Elner S G, Sternberg P, Jr. (2002) Macrophage and retinal pigment epithelium expression of angiogenic cytokines in choroidal neovascularization. Mol Vis 8: 119-126

Hageman G S, Anderson D H, Johnson L V, Hancox L S, Taiber A J, Hardisty L I, Hageman J L, Stockman H A, Borchardt J D, Gehrs K M, Smith R J, Silvestri G, Russell S R, Klaver C C, Barbazetto I, Chang S, Yannuzzi L A, Barile G R, Merriam J C, Smith R T, Olsh A K, Bergeron J, Zernant J, Merriam J E, Gold B, Dean M, Allikmets R (2005) A common haplotype in the complement regulatory gene factor H (HF1/CFH) predisposes individuals to age-related macular degeneration. Proc Natl Acad Sci USA 102: 7227-7232

Hageman G S, Luthert P J, Victor Chong N H, Johnson L V, Anderson D H, Mullins R F (2001) An integrated hypothesis that considers drusen as biomarkers of immune-mediated processes at the RPE-Bruch's membrane interface in aging and age-related macular degeneration. Prog Retin Eye Res 20: 705-732

Hageman G S, Mullins R F (1999) Molecular composition of drusen as related to substructural phenotype. Mol Vis 5: 28

Hageman G S, Mullins R F, Russell S R, Johnson L V, Anderson D H (1999) Vitronectin is a constituent of ocular drusen and the vitronectin gene is expressed in human retinal pigmented epithelial cells. Faseb J 13: 477-484

Haines J L, Hauser M A, Schmidt S, Scott W K, Olson L M, Gallins P, Spencer K L, Kwan S Y, Noureddine M, Gilbert J R, Schnetz-Boutaud N, Agarwal A, Postel E A, Pericak-Vance M A (2005) Complement factor H variant increases the risk of age-related macular degeneration. Science 308: 419-421

Hollyfield J G, Bonilha V L, Rayborn M E, Yang X, Shadrach K G, Lu L, Ufret R L, Salomon R G, Perez V L (2008) Oxidative damage-induced inflammation initiates age-related macular degeneration. Nat Med 14: 194-198

Ischiropoulos H (1998) Biological tyrosine nitration: a pathophysiological function of nitric oxide and reactive oxygen species. Arch Biochem Biophys 356: 1-11

Jha P, Bora P S, Bora N S (2007) The role of complement system in ocular diseases including uveitis and macular degeneration. Mol Immunol 44: 3901-3908

Johnson L V, Ozaki S, Staples M K, Erickson P A, Anderson D H (2000) A potential role for immune complex pathogenesis in drusen formation. Exp Eye Res 70: 441-449

Karwatowski W S, Jeffries T E, Duance V C, Albon J, Bailey A J, Easty D L (1995) Preparation of Bruch's membrane and analysis of the age-related changes in the structural collagens. Br J Ophthalmol 79: 944-952

Klein R, Klein B E, Linton K L (1992) Prevalence of age-related maculopathy. The Beaver Dam Eye Study. Ophthalmology 99: 933-943

Klein R J, Zeiss C, Chew E Y, Tsai J Y, Sackler R S, Haynes C, Henning A K, SanGiovanni J P, Mane S M, Mayne S T, Bracken M B, Ferris F L, Ott J, Barnstable C, Hoh J (2005) Complement factor H polymorphism in age-related macular degeneration. Science 308: 385-389

Laine M, Jarva H, Seitsonen S, Haapasalo K, Lehtinen M J, Lindeman N, Anderson D H, Johnson P T, Jarvela I, Jokiranta T S, Hageman G S, Immonen I, Meri S (2007) Y402H polymorphism of complement factor H affects binding affinity to C-reactive protein. J Immunol 178: 3831-3836

Lyda W, Eriksen N, Krishna N (1957) Studies of Bruch's membrane; flow and permeability studies in a Bruch's membrane-choroid preparation. Am J Ophthalmol 44: 362-369; discussion 369-370

Marietta M A, Yoon P S, Iyengar R, Leaf C D, Wishnok J S (1988) Macrophage oxidation of L-arginine to nitrite and nitrate: nitric oxide is an intermediate. Biochemistry 27: 8706-8711

Mitchell P, Smith W, Attebo K, Wang J J (1995) Prevalence of age-related maculopathy in Australia. The Blue Mountains Eye Study. Ophthalmology 102: 1450-1460

Miyagi M, Sakaguchi H, Darrow R M, Yan L, West K A, Aulak K S, Stuehr D J, Hollyfield J G, Organisciak D T, Crabb J W (2002) Evidence that light modulates protein nitration in rat retina. Mol Cell Proteomics 1: 293-303

Moore D J, Hussain A A, Marshall J (1995) Age-related variation in the hydraulic conductivity of Bruch's membrane. Invest Ophthalmol Vis Sci 36: 1290-1297

Mullins R F, Russell S R, Anderson D H, Hageman G S (2000) Drusen associated with aging and age-related macular degeneration contain proteins common to extracellular deposits associated with atherosclerosis, elastosis, amyloidosis, and dense deposit disease. Faseb J 14: 835-846

Newsome D A, Huh W, Green W R (1987) Bruch's membrane age-related changes vary by region. Curr Eye Res 6: 1211-1221

Paik D C, Dillon J, Galicia E, Tilson M D (2001) The nitrite/collagen reaction: non-enzymatic nitration as a model system for age-related damage. Connect Tissue Res 42: 111-122

Paik D C, Ramey W G, Dillon J, Tilson M D (1997) The nitrite/elastin reaction: implications for in vivo degenerative effects. Connect Tissue Res 36: 241-251

Parish C A, Hashimoto M, Nakanishi K, Dillon J, Sparrow J (1998) Isolation and one-step preparation of A2E and iso-A2E, fluorophores from human retinal pigment epithelium. Proc Natl Acad Sci USA 95: 14609-14613

Pauleikhoff D, Barondes M J, Minassian D, Chisholm I H, Bird A C (1990) Drusen as risk factors in age-related macular disease. Am J Ophthalmol 109: 38-43

Pauleikhoff D, Wojteki S, Muller D, Bornfeld N, Heiligenhaus A (2000) [Adhesive properties of basal membranes of Bruch's membrane. Immunohistochemical studies of age-dependent changes in adhesive molecules and lipid deposits]. Ophthalmologe 97: 243-250.

Rozanowska M, Wessels J, Boulton M, Burke J M, Rodgers M A, Truscott T G, Sarna T (1998) Blue light-induced singlet oxygen generation by retinal lipofuscin in non-polar media. Free Radic Biol Med 24: 1107-1112

Ruberti J W, Curcio C A, Millican C L, Menco B P, Huang J D, Johnson M (2003) Quick-freeze/deep-etch visualization of age-related lipid accumulation in Bruch's membrane. Invest Ophthalmol V is Sci 44: 1753-1759

Schaumberg D A, Christen W G, Buring J E, Glynn R J, Rifai N, Ridker P M (2007) High-sensitivity C-reactive protein, other markers of inflammation, and the incidence of macular degeneration in women. Arch Ophthalmol 125: 300-305

Sellner P A (1986) The movement of organic solutes between the retina and pigment epithelium. Exp Eye Res 43: 631-639

Skerka C, Lauer N, Weinberger A A, Keilhauer C N, Suhnel J, Smith R, Schlotzer-Schrehardt U, Fritsche L, Heinen S, Hartmann A, Weber B H, Zipfel P F (2007) Defective complement control of factor H (Y402H) and FHL-1 in age-related macular degeneration. Mol Immunol 44: 3398-3406

Solberg Y, Rosner M, Belkin M (1998) The association between cigarette smoking and ocular diseases. Surv Ophthalmol 42: 535-547

Streilein J W (2003) Ocular immune privilege: the eye takes a dim but practical view of immunity and inflammation. J Leukoc Biol 74: 179-185

Sun K, Cai H, Tezel T H, Paik D, Gaillard E R, Del Priore L V (2007) Bruch's membrane aging decreases phagocytosis of outer segments by retinal pigment epithelium. Mol Vis 13: 2310-2319

Tezel T H, Del Priore L V, Kaplan H J (2004) Reengineering of aged Bruch's membrane to enhance retinal pigment epithelium repopulation. Invest Ophthalmol Vis Sci 45: 3337-3348

Wang J, Ohno-Matsui K, Yoshida T, Kojima A, Shimada N, Nakahama K, Safranova O, Iwata N, Saido T C, Mochizuki M, Morita I (2008) Altered function of factor I caused by amyloid beta: implication for pathogenesis of age-related macular degeneration from Drusen. J Immunol 181: 712-720

Wang Z, Paik D C, Del Priore L V, Burch R L, Gaillard E R (2005) Nitrite-modified extracellular matrix proteins deleteriously affect retinal pigment epithelial cell function and viability: a comparison study with nonenzymatic glycation mechanisms. Curr Eye Res 30: 691-702

Wu Z, Lauer T W, Sick A, Hackett S F, Campochiaro P A (2007) Oxidative stress modulates complement factor H expression in retinal pigmented epithelial cells by acetylation of FOXO3. J Biol Chem 282: 22414-22425

Yamamoto T, Yamashita H (1989) Scanning electron microscopic observation of Bruch's membrane with the osmium tetroxide treatment. Br J Ophthalmol 73: 162-167.

Yasukawa T, Wiedemann P, Hoffmann S, Kacza J, Eichler W, Wang Y S, Nishiwaki A, Seeger J, Ogura Y (2007) Glycoxidized particles mimic lipofuscin accumulation in aging eyes: a new age-related macular degeneration model in rabbits. Graefes Arch Clin Exp Ophthalmol 245: 1475-1485

What is claimed is:

1. A method of determining that a human has age-related macular degeneration (AMD) and treating AMD, the method comprising:
    (a) quantifying a biomarker in the Bruch's membrane of the human wherein the biomarker comprises nitro-A2E; and
    (b) classifying the human as having AMD if the biomarker is present in quantities above a value in Bruch's membrane of humans without AMD;
    (c) administering a treatment for AMD.

2. The method of claim 1, wherein quantifying the biomarker comprises analyzing fluorescent patterns from the Bruch's membrane with a scanning laser ophthalmoscope.

3. The method of claim 1 wherein quantifying the biomarker comprises measuring intensity of the fluorescent signal from the Bruch's membrane of the human.

4. The method of claim 1 wherein quantifying the biomarker is accomplished with a mass spectrometer.

5. A method of determining efficacy of a treatment for age-related macular degeneration (AMD) in a patient, of the method comprising:
    (a) quantifying biomarkers comprising nitro-A2E in the patient's Bruch's membrane;
    (b) administering a treatment for AMD;
    (c) repeating the quantifying of (a); and
    (d) comparing the quantity of biomarkers before the treatment to the quantity of biomarkers after the treatment to determine the treatment's efficacy, wherein a reduction in the quantity of the biomarkers indicates efficacy.

6. The method of claim 5, wherein the quantifying is performed from analysis of fluorescent patterns of the biomarkers from the Bruch's membrane.

7. A method of determining the presence of AMD in an animal model and treating AMD, the method comprising:
    (a) quantifying nitro-A2E in the animal's Bruch's membrane; and
    (b) determining that the animal has AMD if the quantity of nitro-A2E is above that of a value of nitro-A2E in animals without AMD;
    (c) administering a treatment for AMD.

8. The method of claim 7, further comprising determining the efficacy of a treatment for AMD by administering the treatment, quantifying the amount of nitro A-2E and comparing the amount of nitro-A2E before the treatment to the amount of nitro-A2E after the treatment, from which efficacy is determined.

* * * * *

UNITED STATES PATENT AND TRADEMARK OFFICE
CERTIFICATE OF CORRECTION

PATENT NO. : 9,247,875 B2  
APPLICATION NO. : 12/753394  
DATED : February 2, 2016  
INVENTOR(S) : Elizabeth Gaillard et al.

Page 1 of 1

It is certified that error appears in the above-identified patent and that said Letters Patent is hereby corrected as shown below:

In the claims,

In Column 16, Claim 5, line 38 should read as follows:
--age-related macular degeneration (AMD) in a patient, the--

In Column 16, Claim 8, line 62:
"nitro A-2E" should be corrected to read --nitro-A2E--

Signed and Sealed this
Nineteenth Day of April, 2016

Michelle K. Lee
*Director of the United States Patent and Trademark Office*